United States Patent [19]

Nelson et al.

[11] Patent Number: 5,491,231
[45] Date of Patent: Feb. 13, 1996

[54] HINDERED N-OXIDE ESTERS OF RAPAMYCIN

[75] Inventors: Frances C. Nelson; Guy A. Schiehser, both of Yardley, Pa.

[73] Assignee: American Home Products Corporation, Madison, N.J.

[21] Appl. No.: 345,972

[22] Filed: Nov. 28, 1994

[51] Int. Cl.[6] .................. A61K 31/395; C02D 491/06
[52] U.S. Cl. .................................................. 540/456
[58] Field of Search ............................................. 540/456

[56]  References Cited

U.S. PATENT DOCUMENTS

| | | | |
|---|---|---|---|
| 3,205,234 | 9/1965 | Schummann | 540/338 |
| 3,929,992 | 12/1975 | Sehgal et al. | 424/122 |
| 3,993,749 | 11/1976 | Sehgal et al. | 424/122 |
| 4,316,885 | 2/1982 | Rakhit | 424/122 |
| 4,375,464 | 3/1983 | Sehgal et al. | 424/122 |
| 4,401,653 | 8/1983 | Eng | 424/122 |
| 4,650,803 | 3/1987 | Stella et al. | 514/291 |
| 4,885,171 | 12/1989 | Surendra et al. | 424/122 |
| 5,023,262 | 6/1991 | Caufield et al. | 514/291 |
| 5,023,263 | 6/1991 | Von Burg | 514/291 |
| 5,023,264 | 6/1991 | Caufield et al. | 514/291 |
| 5,078,999 | 1/1992 | Warner et al. | 514/291 |
| 5,080,899 | 1/1992 | Sturm et al. | 514/291 |
| 5,091,389 | 2/1992 | Ondeyka et al. | 514/291 |
| 5,100,883 | 3/1992 | Schiehser | 514/291 |
| 5,100,899 | 3/1992 | Calne | 514/291 |
| 5,102,876 | 4/1992 | Caufield | 540/546 |
| 5,118,677 | 6/1992 | Caufield | 540/456 |
| 5,118,678 | 6/1992 | Kao et al. | 540/456 |
| 5,120,842 | 6/1992 | Failli et al. | 540/456 |
| 5,130,307 | 7/1992 | Failli et al. | 540/456 |
| 5,138,051 | 8/1992 | Hughes et al. | 540/456 |
| 5,151,413 | 9/1992 | Caufield et al. | 540/456 |
| 5,169,851 | 12/1992 | Hughes et al. | 514/291 |
| 5,177,203 | 1/1993 | Failli et al. | 540/456 |
| 5,194,447 | 3/1993 | Kao | 540/456 |
| 5,221,670 | 7/1993 | Caufield | 540/456 |
| 5,233,036 | 8/1993 | Hughes | 540/456 |
| 5,260,300 | 11/1993 | Hu | 514/291 |
| 5,302,584 | 4/1994 | Kao et al. | 514/291 |
| 5,385,908 | 1/1995 | Nelson et al. | 514/291 |
| 5,385,909 | 1/1995 | Nelson et al. | 514/291 |
| 5,385,910 | 1/1995 | Ocain et al. | 514/291 |

FOREIGN PATENT DOCUMENTS

507555A1  7/1992  European Pat. Off. ............... 514/291

OTHER PUBLICATIONS

Venzina, C., J. Antibiot. 28:721 (1975).
Sehgal, S. N., J. Antibiot. 28:727 (1975).
Baker, H. J., Antibiot. 31:539 (1978).
Martel, R. R., Can. J. Physiol. Pharmacol. 55:48 (1977).
Staruch, M. J., FASEB 3:3411 (1989).
Dumont, F. J., FASEB 3:5256 (1989).
Calne, R. Y., Lancet 1183 (1978).
Morris, R. E., Med. Sci. Res. 17:877 (1989).
Baeder, W. L., Fifth Int. Conf. Inflamm. Res. Assoc. 121 (Abstract) (1990).
Meiser, B. M., J. Heart Lung Transplant. 11 (pt. 2):197 (1992).
Stepkowski, S. M., Transplantation Proc. 23:507 (1991).

*Primary Examiner*—Robert T. Bond
*Attorney, Agent, or Firm*—Arnold S. Milowsky

[57]  ABSTRACT

A compound of the structure

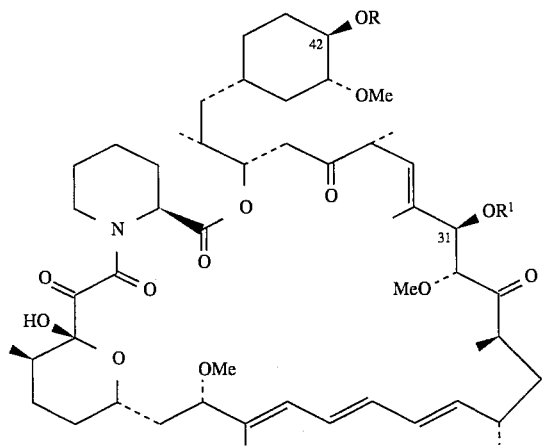

wherein R and $R^1$ are each, independently,

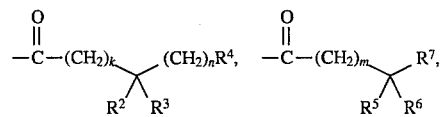

or hydrogen;

$R^2$ and $R^3$ are each, independently, alkyl, arylalkyl, or $R^2$ and $R^3$ may be taken together to form a cycloalkyl ring;

$R^4$ is a heterocyclic N-oxide radical, which may be optionally substituted;

$R^5$ is alkyl or arylalkyl;

$R^6$ and $R^7$ are taken together to form a saturated N-alkyl-heterocyclic N-oxide, which may be optionally substituted;

k=0–1, m=0–1;

n=1–6;

with the proviso that R and $R^1$ are not both hydrogen, which is useful as an immunosuppressive, antiinflammatory, antifungal, antiproliferative, and antitumor agent.

7 Claims, No Drawings

HINDERED N-OXIDE ESTERS OF RAPAMYCIN

BACKGROUND OF THE INVENTION

This invention relates to hindered N-oxide esters of rapamycin and a method for using them for inducing immunosuppression, and in the treatment of transplantation rejections, graft vs. host disease, autoimmune diseases, diseases of inflammation, adult T-cell leukemia/lymphoma, solid tumors, fungal infections, and hyperproliferative vascular disorders.

Rapamycin is a macrocyclic triene antibiotic produced by *Streptomyces hygroscopicus*, which was found to have antifungal activity, particularly against *Candida albicans*, both in vitro and in vivo [C. Vezina et al., J. Antibiot. 28, 721 (1975); S. N. Sehgal et al., J. Antibiot. 28, 727 (1975); H. A. Baker et al., J. Antibiot. 31,539 (1978); U.S. Pat. No. 3,929,992; and U.S. Pat. No. 3,993,749].

Rapamycin alone (U.S. Pat. No. 4,885,171) or in combination with picibanil (U.S. Pat. No. 4,401,653) has been shown to have antitumor activity. R. Martel et al. [Can. J. Physiol. Pharmacol. 55, 48 (1977)] disclosed that rapamycin is effective in the experimental allergic encephalomyelitis model, a model for multiple sclerosis; in the adjuvant arthritis model, a model for rheumatoid arthritis; and effectively inhibited the formation of IgE-like antibodies.

The immunosuppressive effects of rapamycin have been disclosed in FASEB 3, 3411 (1989). Cyclosporin A and FK-506, other macrocyclic molecules, also have been shown to be effective as immunosuppressive agents, therefore useful in preventing transplant rejection [FASEB 3, 3411 (1989); FASEB 3, 5256 (1989); R. Y. Calne et al., Lancet 1183 (1978); and U.S. Pat. No. 5,100,899].

Rapamycin has also been shown to be useful in preventing or treating systemic lupus erythematosus [U.S. Pat. No. 5,078,999], pulmonary inflammation [U.S. Pat. No. 5,080, 8991, insulin dependent diabetes mellitus [Fifth Int. Conf. Inflamm. Res. Assoc. 121 (Abstract), (1990)], smooth muscle cell proliferation and intimal thickening following vascular injury [Monks, R. J. Heart Lung Transplant 11 (pt. 2): 197 (1992)], adult T-cell leukemia/lymphoma [European Patent Application 525,960 A1], and ocular inflammation [European Patent Application 532,862 A1].

Mono- and diacylated derivatives of rapamycin (esterified at the 28 and 43 positions) have been shown to be useful as antifungal agents (U.S. Pat. No. 4,316,885) and used to make water soluble aminoacyl prodrugs of rapamycin (U.S. Pat. No. 4,650,803). Recently, the numbering convention for rapamycin has been changed; therefore according to Chemical Abstracts nomenclature, the esters described above would be at the 31- and 42- positions.

DESCRIPTION OF THE INVENTION

This invention provides derivatives of rapamycin which are useful as immunosuppressive, antiinflammatory, antifungal, antiproliferative, and antitumor agents having the structure

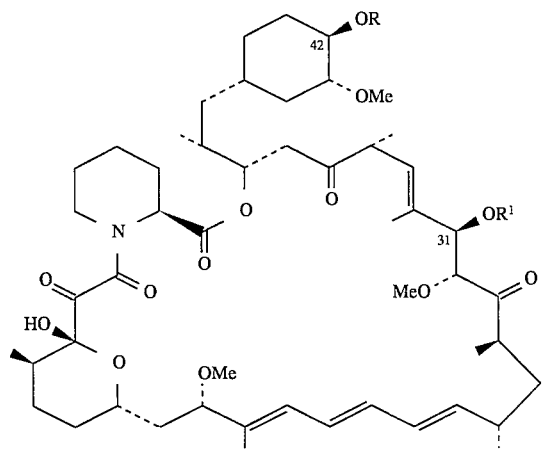

wherein R and $R^1$ are each, independently,

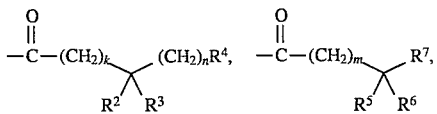

or hydrogen;

1 $R^2$ and $R^3$ are each, independently, alkyl of 1–6 carbon atoms, arylalkyl of 7–10 carbons, or $R^2$ and $R^3$ may be taken together to form a cycloalkyl ring of 3–8 carbon atoms;

$R^4$ is a heterocyclic N-oxide radical of 5–12 atoms, which may be optionally mono-, di-, or tri- substituted with a group selected from alkyl of 1–6 carbon atoms, arylalkyl of 7–10 carbon atoms, alkoxy of 1–6 carbon atoms, cyano, halo, hydroxy, nitro, carbalkoxy of 2–7 carbon atoms, trifluoromethyl, trifluoromethoxy, hydroxyalkyl of 1–6 carbon atoms, alkoxyalkyl of 2–12 carbon atoms, $-SO_3H$, $-PO_3H_2$, and $-CO_2H$;

$R^5$ is alkyl of 1–6 carbon atoms or arylalkyl of 7–10 carbon atoms;

$R^6$ and $R^7$ are taken together to form a saturated N-alkyl of 1–6 carbon atoms-heterocyclic N-oxide of 5–8 ring atoms, which may be optionally mono, di-, or tri-substituted with a group selected from alkyl of 1–6 carbon atoms, aroyl of 3– 11 carbon atoms, and perfluoroalkyl of 1–6 carbon atoms;

k=0–1,
m=0–1;
n=1–6;
with the proviso that R and $R^1$ are not both hydrogen.

It is preferred that the heterocyclic N-oxide radical defined in $R^4$ be an unsaturated or partially saturated heterocyclic N-oxide radical of 5–12 atoms having 1 ring or 2 fused rings. Preferred heterocyclic N-oxide radicals include unsaturated heterocyclic N-oxide radicals such as 1-methyl-pyrazolyl-2-N-oxide, imidazolyl-3-N-oxide, 1,2,3-triazolyl 2- or 3-N-oxide, 1,2,4-triazolyl 2- or 4-N-oxide, 1,2,5oxa-diazolyl N-oxide, 1,2,3,5-oxatriazolyl N-oxide, pyridinyl N-oxide, pyridazinyl N-oxide, pyrimidinyl N-oxide, pyrazinyl N-oxide, 1,3,5-triazinyl N-oxide, 1,2,4-triazinyl N-oxide, 1,2,3-triazinyl N-oxide, 1,2,4-diazepinyl N-oxide, 2-isobenzazolyl N-oxide, 1,5-pyrindinyl N-oxide, benzpyrazolyl N-oxide, benzisoxazolyl N-oxide, benzoxazolyl N-oxide, quinolinyl N-oxide, isoquinolinyl N-oxide, cinnolinyl N-oxide, quinazolinyl N-oxide, naphthyridinyl N-oxide, pyrido[3,4-b]pyridinyl N-oxide, pyrido[4,3-b] pyridinyl N-oxide, pyrido[2,3-b]pyridinyl N-oxide, 1,4,2-benzoxazinyl N-oxide, 2,3,1-benzoxazinyl N-oxide, carbazolyl N-oxide, purinyl N-oxide, and partially saturated heterocyclic N-oxide radicals selected from the list above. All of the preferred heterocyclic N-oxide radicals contain at least one double bond. When the heterocyclic N-oxide radical is partially saturated, one or more of the olefins in the unsaturated ring system is saturated; the partially saturated heterocyclic N-oxide radical still contains at least one double bond. The —(CH$_2$)$_n$— sidechain can be attached to any position of the heterocyclic N-oxide radical containing a carbon or nitrogen capable of forming a bond with the —(CH$_2$)$_n$— sidechain. More preferred heterocyclic N-oxide radicals are pyridinyl N-oxide, pyrazinyl N-oxide, triazinyl N-oxide, pyrimidinyl N-oxide, pyridazinyl N-oxide, imidazolyl N-oxide, pyrazolyl N-oxide, quinolinyl N-oxide, and isoquinolinyl N-oxide. Pyridinyl N-oxide is the most preferred heterocyclic N-oxide radical.

It is preferred that the saturated heterocyclic N-alkyl of 1–6 carbon atoms, N-oxide of 5–8 ring atoms as defined by R$^6$ and R$^7$ is a N-alkyl of 1–6 carbon atoms-piperidine N-oxide, N-alkyl of 1–6 carbon atoms-morpholine N-oxide, N-alkyl of 1–6 carbon atoms-piperazine N-oxide, N-alkyl of 1–6 carbon atoms-pyrazolidine N-oxide, N-alkyl of 1–6 carbon atoms-imidazolidine N-oxide, or N-alkyl of 1–6 carbon atoms-pyrrolidine N-oxide group. Methyl is the preferred alkyl group.

Aroyl is defined as the radical Ar-CO— where Ar is an aryl radical. It is preferred that the aryl moiety of the arylalkyl group and aroyl group is a phenyl, naphthyl, pyridinyl, quinolinyl, isoquinolinyl, furanyl, benzofuranyl, benzodioxyl, benzoxazolyl, benzoisoxazolyl, indolyl, isoxazolyl, pyrimidinyl, pyrazinyl, benzopyranyl, or benzimidazolyl group which may be optionally mono-, di-, or tri-substituted with a group selected from alkyl of 1–6 carbon atoms, alkoxy of 1–6 carbon atoms, cyano, halo, hydroxy, nitro, carbalkoxy of 2–7 carbon atoms, trifluoromethyl, hydroxyalkyl of 1–6 carbon atoms, alkoxyalkyl of 2–12 carbon atoms, —SO$_3$H, —PO$_3$H$_2$, and —CO$_2$H. It is more preferred that the aryl moiety is a phenyl group that may be optionally substituted as described above. The term alkyl of 1–6 carbon atoms includes both straight chain as well as branched carbon chains.

Of the compounds of this invention, preferred members are those in which R$^1$ is hydrogen; those in which R$^1$ is hydrogen and R is

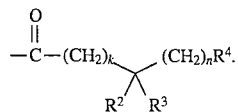

When R is

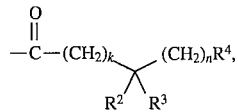

and R$^1$ is hydrogen, preferred compounds are those in which R$^4$ are pyridinyl N-oxide, pyrazinyl N-oxide, triazinyl N-oxide, pyrimidinyl N-oxide, pyridazinyl N-oxide, imidazolyl N-oxide, pyrazolyl N-oxide, quinolinyl N-oxide, or isoquinolinyl N-oxide; those in which R$^4$ is pyridinyl N-oxide; those in which R$^4$ is pyridinyl N-oxide, and k=0; those in which R$^4$ is pyridinyl N-oxide, k=0, and R$^2$ and R$^3$ are alkyl of 1–6 carbon atoms or are taken together to form a cycloalkyl ring of 3–8 carbon atoms.

Compounds which contain the ester group

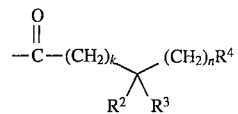

at the 42- or 31,42-positions can be prepared by treating a suitably substituted carboxylic acid with a hindered base such as LDA, followed by alkylation with a haloalkyl-nitrogen containing heterocycle. The nitrogen containing heterocyclic moiety can be oxidized to the corresponding N-oxide using an oxidizing agent such as m-chloroperbenzoic acid (MCPBA). The resulting alkylated acid can then be activated as a mixed anhydride, with an acylating group such as 2,4,6-trichlorobenzoyl chloride. Treatment of rapamycin with the mixed anhydride under mildly basic condition provides the desired compounds. Mixtures of 42- and 31,42-esters can be separated by chromatography. This scheme is outlined below. The starting acids and haloalkyl-heterocycles are either commercially available or can be prepared by standard literature procedures.

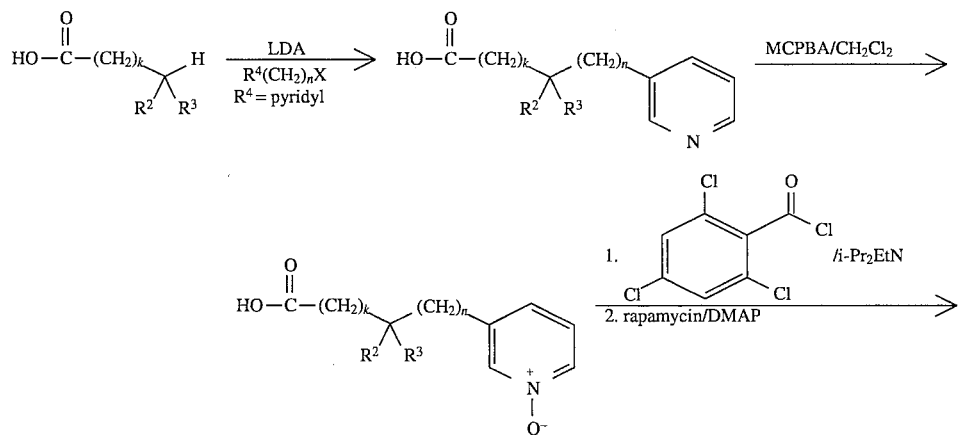

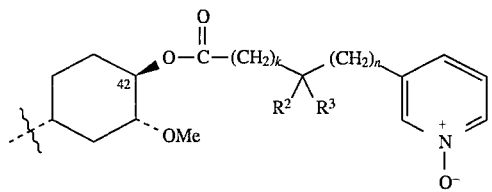

Compounds which contain the ester group

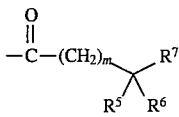

at the 42- or 31,42-positions can be prepared analogously. Mixtures of 42- and 31,42-esters can be separated by chromatography.

The 31-esters of this invention can be prepared by protecting the 42-alcohol of rapamycin with a protecting group, such as with a tert-butyl dimethylsilyl group, followed by esterification of the 31-position by the procedures described above. The preparation of rapamycin 42-silyl ethers is described in U.S. Pat. No. B1 5,120,842, which is hereby incorporated by reference. Removal of the protecting group provides the 31-esterified compounds. In the case of the tert-butyl dimethylsilyl protecting group, deprotection can be accomplished under mildly acidic conditions, such as acetic acid/water/THF. The deprotection procedure is described in Example 15 of U.S. Pat. No. 5,118,678, which is hereby incorporated by reference.

Having the 31-position esterified and the 42-position deprotected, the 42-position can be esterified using a different acylating agent than was reacted with the 31-alcohol. to give compounds having different esters at the 31- and 42-positions. Alternatively, the 42-esterified compounds, prepared as described above, can be reacted with a different acylating agent to provide compounds having different esters at the 31- and 42-positions.

This invention also covers analogous hindered esters of other rapamycins such as, but not limited to, 29-demethoxyrapamycin, [U.S. Pat. No. 4,375,464, 32-demethoxyrapamycin under C. A. nomenclature]; rapamycin derivatives in which the double bonds in the 1-, 3-, and/or 5-positions have been reduced [U.S. Pat. No. 5,023,2621; 29-desmethylrapamycin [U.S. Pat. No. 5,093,339, 32-desmethylrapamycin under C. A. nomenclature]; 7,29-bisdesmethylrapamycin [U.S. Pat. No. 5,093,338, 7,32-desmethylrapamycin under C. A. nomenclature]; and 15-hydroxyrapamycin [U.S. Pat. No. 5,102,876]. This invention also covers hindered esters at the 31-position of 42-oxorapamycin [U.S. Pat. No. 5,023,263]. The disclosures in the above cited U.S. Patents are hereby incorporated by reference.

Immunosuppressive activity for representative compounds of this invention was evaluated in an in vitro standard pharmacological test procedure to measure lymphocyte proliferation (LAF) and in an in vivo standard pharmacological test procedure that measures the immunosuppressive activity of the compound tested as well as the ability of the compound tested to inhibit or treat transplant rejection. The procedures for these standard pharmacological test procedures are provided below.

The comitogen-induced thymocyte proliferation procedure (LAF) was used as an in vitro measure of the immunosuppressive effects of representative compounds. Briefly, cells from the thymus of normal BALB/c mice are cultured for 72 hours with PHA and IL-1 and pulsed with tritiated thymidine during the last six hours. Cells are cultured with and without various concentrations of rapamycin, cyclosporin A, or test compound. Cells are harvested and incorporated radioactivity is determined. Inhibition of lymphoproliferation is assessed as percent change in counts per minute from non-drug treated controls. For each compound evaluated, rapamycin was also evaluated for the purpose of comparison. An $IC_{50}$ was obtained for each test compound as well as for rapamycin. When evaluated as a comparator for the representative compounds of this invention, rapamycin had an $IC_{50}$ of 2.4 nM. The results obtained are provided as an $IC_{50}$.

Representative compounds of this invention were also evaluated in an in vivo test procedure designed to determine the survival time of pinch skin graft from male BALB/c donors transplanted to male $C_3H$(H-2K) recipients. The method is adapted from Billingham R. E. and Medawar P. B., J. Exp. Biol. 28:385–402, (1951). Briefly, a pinch skin graft from the donor was grafted on the dorsum of the recipient as a allograft. and an isograft was used as control in the same region. The recipients were treated with either varying concentrations of test compounds intraperitoneally or orally. Rapamycin was used as a test control. Untreated recipients serve as rejection control. The graft was monitored daily and observations were recorded until the graft became dry and formed a blackened scab. This was considered as the rejection day. The mean graft survival time (number of days ±S.D.) of the drug treatment group was compared with the control group. The following table shows the results that were obtained. Results are expressed as the mean survival time in days. Untreated (control) pinch skin grafts are usually rejected within 6–7 days. Compounds were tested using a dose of 4 mg/kg administered i.p. or using a dose of 40 mg/kg administered p.o.

The results obtained in these standard pharmacological test procedures are provided following the procedure for making the specific compounds that were tested.

The results of these standard pharmacological test procedures demonstrate immunosuppressive activity both in vitro and in vivo for the compounds of this invention. The results obtained in the LAF test procedure indicates suppression of T-cell proliferation, thereby demonstrating the immunosuppressive activity of the compounds of this invention. Further demonstration of the utility of the compounds of this invention as immunosuppressive agents was shown by the results obtained in the skin graftstandard pharmacological test procedure. Additionally, the results obtained in the skin graft test procedure further demonstrates the ability of the compounds of this invention to treat or inhibit transplantation rejection.

Based on the results of these standard pharmacological test procedures, the compounds are useful in the treatment or inhibition of transplantation rejection such as kidney, heart, liver, lung, bone marrow, pancreas (islet cells), cornea, small bowel, and skin allografts, and heart valve xenografts; in the treatment or inhibition of autoimmune diseases such as lupus, rheumatoid arthritis, diabetes mellitus, myasthenia gravis, and multiple sclerosis; and diseases of inflammation such as psoriasis, dermatitis, eczema, seborrhea, inflammatory bowel disease, and eye uveitis.

Because of the activity profile obtained, the compounds of this invention also are considered to have antitumor, antifungal activities, and antiproliferative activities. The compounds of this invention therefore also useful in treating solid tumors, adult T-cell leukemiaJlymphoma, fungal infections, and hyperproliferative vascular diseases such as restenosis and atherosclerosis.

When administered for the treatment or inhibition of the above disease states, the compounds of this invention can be administered to a mammal orally, parenterally, intranasally, intrabronchially, transdermally, topically, intravaginally, or rectally.

It is contemplated that when the compounds of this invention are used as an immunosuppressive or antiinflammatory agent, they can be administered in conjunction with one or more other immunoregulatory agents. Such other immunoregulatory agents include, but are not limited to azathioprine, corticosteroids, such as prednisone and methylprednisolone, cyclophosphamide, rapamycin, cyclosporin A, FK-506, OKT-3, and ATG. By combining the compounds of this invention with such other drugs or agents for inducing immunosuppression or treating inflammatory conditions, the lesser amounts of each of the agents am required to achieve the desired effect. The basis for such combination therapy was established by Stepkowski whose results showed that the use of a combination of rapamycin and cyclosporin A at subtherapeutic doses significantly prolonged heart allograft survival time. [Transplantation Proc. 23: 507 ( 1991 )].

The compounds of this invention can be formulated neat or with a pharmaceutical carrier to a mammal in need thereof. The pharmaceutical carrier may be solid or liquid. When formulated orally, it has been found that 0.01% Tween 80 in PHOSAL PG-50 (phospholipid concentrate with 1,2-propylene glycol, A. Nattermann & Cie. GmbH) provides an acceptable oral formulation.

A solid carrier can include one or more substances which may also act as flavoring agents, lubricants, solubilizers, suspending agents, fillers, glidants, compression aids, binders or tablet-disintegrating agents; it can also be an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the carrier can also be an oily ester such as ethyl oleate and isopropyl myristate. Sterile liquid carriers are useful in sterile liquid form compositions for parentoral administration. The liquid carrier for pressurized compositions can be halogenated hydrocarbon or other pharmaceutically acceptable propellant.

Liquid pharmaceutical compositions which are sterile solutions or suspensions can be utilized by, for example, intramuscular, intraperitoneal or subcutaneous injection. Sterile solutions can also be administered intravenously. The compound can also be administered orally either in liquid or solid composition form.

The compounds of this invention may be administered rectally in the form of a conventional suppository. For administration by intranasal or intrabronchial inhalation or insufflation, the compounds of this invention may be formulated into an aqueous or partially aqueous solution, which can then be utilized in the form of an aerosol. The compounds of this invention may also be administered transdermally through the use of a transdermal patch containing the active compound and a carrier that is inert to the active compound, is non toxic to the skin, and allows delivery of the agent for systemic absorption into the blood stream via the skin. The carrier may take any number of forms such as creams and ointments, pastes, gels, and occlusive devices. The creams and ointments may be viscous liquid or semisolid emulsions of either the oil-in-water or water-in-oil type. Pastes comprised of absorptive powders dispersed in petroleum or hydrophilic petroleum containing the active ingredient may also be suitable. A variety of occlusive devices may be used to release the active ingredient into the blood stream such as a semipermeable membrane covering a reservoir containing the active ingredient with or without a carrier, or a matrix containing the active ingredient. Other occlusive devices are known in the literature.

In addition, the compounds of this invention may be employed as a solution, cream, or lotion by formulation with pharmaceutically acceptable vehicles containing (0.1–5 percent, preferably 2%, of active compound which may be administered to a lungally affected area.

The dosage requirements vary with the particular compositions employed, the route of administration, the severity of the symptoms presented and the particular subject being treated. Based on the results obtained in the standard pharmacological test procedures, projected daily dosages of active compound would be 0.1 µg/kg–100 mg/kg, preferably between 0.001–25 mg/kg, and more preferably between 0.01–5 mg/kg. Treatment will generally be initiated with small dosages less than the optimum dose of the compound. Thereafter the dosage is increased until the optimum effect under the circumstances is reached; precise dosages for oral, parenteral, nasal, or intrabronchial administration will be determined by the administering physician based on experience with the individual subject treated. Preferably, the pharmaceutical composition is in unit dosage form, e.g. as tablets or capsules. In such form, the composition is subdivided in unit dose containing appropriate quantities of the active ingredient; the unit dosage forms can be packaged compositions, for example, packeted powders, vials, ampoules, prefilled syringes or sachets containing liquids. The unit dosage form can be, for example, a capsule or tablet itself, or it can be the appropriate number of any such compositions in package form.

The following examples illustrate the preparation and biological activities of representative compounds of this invention.

EXAMPLE 1

2.2-Dimethyl-3-(3-pyridinyl) propionic acid

Sodium hydride (4.38 g, 110 mmol, 60% dispersion, washed 2× with hexanes and dried under $N_2$) was suspended in THF (140 mL). To this suspension was added diisopropylamine (15.4 mL, 110 mmol). Isobutyric acid (9.27 mL, 100 mmol) was added slowly dropwise. The resulting thick white suspension was heated at a gentle reflux for 20 rain and was then cooled to 0° C. n-Butyllithium (40 mL, 2.5M in hexanes) was added dropwise. The reaction was warmed to room temperature and then to 35° C. for 30 min. The reaction was cooled back to 0° C. and 3-picolyl chloride was quickly added. (The 3-picolyl chloride was obtained by neutralization of the hydrochloride with $NaHCO_3$ and extracted 3× with hexane. The hexane solution was dried over $Na_2SO_4$ and concentrated to provide the free base (caution: lacrymator). All of the hexane was not removed as the free base is somewhat unstable in concentrated form). The reaction was allowed to slowly warm to room temperature and stirred overnight. The reaction was quenched with $H_2O$, the aqueous layer separated and washed 2× with ether. The aqueous layer was then acidified to pH 3 with 6N HCl and again washed 2× ether. The aqueous phase was neutralized with $NaHCO_3$ and extracted 4× ethyl acetate. The organic extracts were combined, dried over $Na_2SO_4$, filtered and concentrated to provide a sticky solid which was triturated with ethyl acetate to provide 1.02 g of the desired product as a tan solid.

EXAMPLE 2

2,2-Dimethyl-3-(3-pyridinyl) propionic acid N-oxide

To a solution of 2,2-dimethyl-3-(3-pyridinyl) propionic acid (2.0 g, 11.17 mmol) in $CHCl_3$ (48 mL) was added MCPBA (4.1 g, 13.07 mmol, 50% wt.). The solution was stirred for 2.5 h and then concentrated in vacuo. The residue was purified via flash column chromatography using 2–20% MeOH in $CH_2Cl_2$ as eluant to provide 2,2-dimethyl-3-(3-pyridinyl) propionic acid N-oxide (1.88 g, 86%) as a white powder. $^1$H NMR (200 MHz, DMSO) δ1.0 (s, 6 H), 2.60 (s, 2 H), 7.10 (m, 1 H), 7.30 (m, 1 H), 8.00 (s, 1 H), 8.05 (d, 1 H), 12.5 (s, 1 H). mp=177°–180 ° C.

EXAMPLE 3

Rapamycin 42-ester with 2.2-dimethyl-3-(3-pyridinyl) propionic acid N-oxide

To a solution of 2,2-dimethyl-3-(3-pyridinyl) propionic acid N-oxide (1.02 g, 5.25 mmol) in THF (36 mL) was added N,N-diisopropylethylamine (0.67g, 5.25 mmol) followed by trichlorobenzoyl chloride (1.22 g, 5.02 mmol). The solution was stirred for 2 h, and the solvent removed via a stream of $N_2$. Benzene (35 mL) was added followed by rapamycin (3.0 g, 3.28 mmol) and DMAP (0.64 g, 5.25 mmol). The reaction was stirred overnight and then quenched with $NaHCO_3$ (sat). The aqueous solution was exctacted with EtOAc, dried over $Na_2SO_4$ concentrated and purified via flash column chromatography using 1–5% MeOH in $CH_2Cl_2$ as eluant followed by recrystallization from $EtOH/H_2O$ to provide 1.35 g, 38% of the title compound. mp=183° C. IR (KBr) 1100 (m), 1160 (m), 1190 (m), 1275 (m), 1300 (m), 1325 (m), 1375 (m), 1450 (s), 1630 (s), 1725 (s), 2920 (s), 3420 (s); 1H NMR (400 MHz, CDCl$_3$) δ0.80–1.95 (comp m, 21 H), 0.91 (d, superimp on comp m, J= 6.81 Hz, 3 H), 0.95 (d, superimp on comp m, J=6.37 Hz, 3 H), 0.99 (d, superimp on comp m, J=6.37 Hz, 3 H), 1.05 (d, superimp on comp m, J=6.59 Hz, 3 H), 1.09 (d, superimp on comp m, J=6.81 Hz, 3 H), 1.17 (s, superimp on comp m, 3 H), 1.24 (s, superimp on comp m, 3 H), 1.65 (s, superimp on comp m, 3 H), 1.76 (s, superimp on comp m, 3 H), 2.11 (m, 4 H), 2.32 (m, 3 H), 2.59 (d, J=6.37 Hz, 1 H), 2.76 (m, 2 H), 2.87 (m, 1 H), 3.12–3.42 (comp m, 3 H), 3.14 (s, superimp on comp m, 3 H), 3.33 (s, superimp on comp m, 6 H), 3.57 (m, 1 H), 3.68 (m, 1 H), 3.75 (d, J = 5.71 Hz, 1 H), 3.86 (m, 1 H), 4.19 (d, J = 5.93 Hz, I H), 4.66 (m, 1 H), 4.77 (s, 1 H), 5.16 (m, 1 H), 5.29 (m, 1 H), 5.41 (d, J= 10.11 Hz, 1 H), 5.53 (dd,J=8.79 15.16 Hz, 1 H), 5.97 (d, J = 10.55 Hz, 1 H), 6.13 (dd, J = 9.89, 15.16 Hz, 1 H), 6.33 (m, 2 H), 7.18 (s, 2 H), 8.10 (s, 2 H); $^{13}$C (100 MHz, CDCl$_3$) δ10.16, 13.22, 13.66, 15.87, 15.92, 16.24, 20.66, 21.49, 24.77, 25.58, 27.23, 29.63, 31.19, 32.81, 33.17, 33.77, 35.10, 35.70, 38.31, 38.94, 40.19, 40.49, 40.89, 41.51, 42.74, 43.33, 44.22, 46.60, 51.27, 55.89, 56.26, 57.09, 59.29, 67.18, 75.38, 76.36, 77.16, 80.97, 84.30, 84.40, 84.71, 86.34, 98.46, 125.25, 126.53, 128.13, 129.47, 130.17, 133.57, 135.67, 136.04, 137.34, 140.09, 140.34, 140.71, 166.74, 169.25, 175.81,192.63, 208.22, 215.29; high resolution mass spectrum (negative ion FAB) m/z 1090.7 [(M--); calcd for $C_{61}H_{90}N_2O_{15}$: 1091.39].

Results obtained in standard pharmacological test procedures:

LAF $IC_{50}$:2.9 nM

Skin graft survival: i.p.: 11.17±0.98 days; oral: 11±0.89 days.

What is claimed is:

1. A compound of the structure

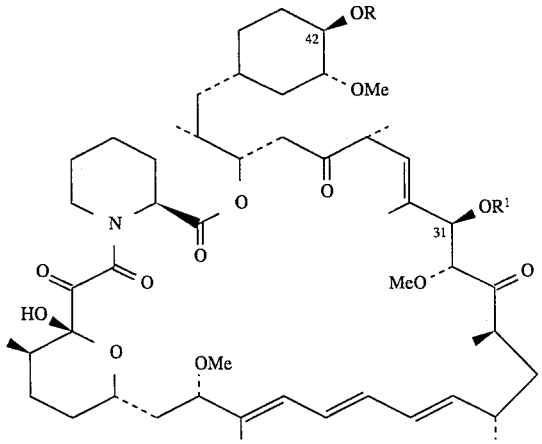

wherein R and $R^1$ are each, independently,

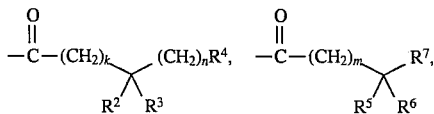

or hydrogen;

$R^2$ and $R^3$ are each independently, alkyl of 1–6 carbon atoms, arylalkyl of 7–10 carbons, or $R^2$ and $R^3$ may be taken together to form a cycloalkyl ring of 3–8 carbon atoms;

$R^4$ is a heterocyclic N-oxide radical selected from the group consisting of 1-methyl-pyrazolyl- 2-N-oxide, imidazoyl-3-N-oxide, 1,2,3-triazolyl 2- or 3-N-oxide, 1,2,4-triazolyl 2- or 4-N-oxide, 1,2,5-oxadiazolyl N-oxide, 1,2,3,5-oxatriazolyl N-oxide, pyridinyl N-oxide, pyridazinyl N-oxide, pyrimidinyl N-oxide, pyrazinyl N-oxide, 1,3,5-triazinyl N-oxide, 1,2,4-triazinyl N-oxide, 1,2,3-triazinyl N-oxide, 1,2,4-diazepinyl N-oxide, 2-isobenzazolyl N-oxide, 1,5-pyrindinyl N-oxide, benzpyrazolyl N-oxide, benzisoxazolyl N-oxide, benzoxazolyl N-oxide, quinolinyl N-oxide, isoquinolinyl N-oxide, cinnolinyl N-oxide, quinazolinyl N-oxide, naphthyridinyl N-oxide, pyrido[3,4-b] pyridinyl N-oxide, pyrido[4,3-b]pyridinyl N-oxide, pyrido[2.3-b]pyridinyl N-oxide, 1,4,2-benzoxazinyl N-oxide, 2,3,1-benzoxazinyl N-oxide, carbazolyl N-oxide, and purinyl N-oxide, which may be optionally mono-, di-, or tri- substituted with a group selected from alkyl of 1–6 carbon atoms, arylalkyl of 7–10 carbon atoms, alkoxy of 1–6 carbon atoms, cyano, halo, hydroxy, nitro, carbalkoxy of 2–7 carbon atoms, trifluoromethyl, trifluoromethoxy, hydroxyalkyl of 1–6 carbon atoms, alkoxyalkyl of 2–12 carbon atoms, —SO$_3$H, —PO$_3$H$_2$, and —CO$_2$H;

R$^5$ is alkyl of 1–6 carbon atoms or arylalkyl of 7–10 carbon atoms;

R$^6$ and R$^7$ are taken together to form a saturated N-alkyl of 1–6 carbon atoms-heterocyclic N-oxide of 5–8 ring atoms, which may be optionally mono-, di-, or tri-substituted with a group selected from alkyl of 1–6 carbon atoms, aroyl of 3–11 carbon atoms, and perfluoroalkyl of 1–6 carbon atoms;

k=0–1, m=0–1;

n=1–6;

with the proviso that R and R$^1$ are not both hydrogen.

2. The compound of claim 1, wherein R$^1$ is hydrogen.

3. The compound of claim 2, wherein R is

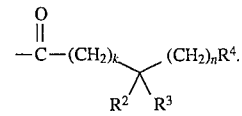

4. The compound of claim 3, wherein R$^4$ is pyridinyl N-oxide, pyrazinyl N-oxide, triazinyl N-oxide, pyrimidinyl N-oxide, pyridazinyl N-oxide, imidazolyl N-oxide, pyrazolyl N-oxide, quinolinyl N-oxide, or isoquinolinyl N-oxide.

5. The compound according to claim 4, wherein R$^4$ is pyridinyl N-oxide.

6. The compound according to claim 5, wherein k=0.

7. The compound according to claim 1 which is rapamycin 42-ester with 2,2-dimethyl- 3-(3-pyridinyl) propionic acid N-oxide.

* * * * *